United States Patent [19]
Wright

[11] Patent Number: 4,777,948
[45] Date of Patent: Oct. 18, 1988

[54] SURGICAL TOOL

[76] Inventor: David W. Wright, 31315 Tamarack, No. 1315, Wixom, Mich. 48096

[21] Appl. No.: 570,763

[22] Filed: Jan. 16, 1984

[51] Int. Cl.⁴ .............................................. A61B 17/32
[52] U.S. Cl. .................................................... 128/312
[58] Field of Search ............... 128/305, 310, 312, 318; 30/130, 291, 292

[56] References Cited

U.S. PATENT DOCUMENTS

| | | | |
|---|---|---|---|
| 1,040,523 | 10/1912 | De Vilbiss . | |
| 3,752,161 | 8/1973 | Bent | 128/312 |
| 3,902,498 | 9/1975 | Niederer | 128/305 |
| 4,201,213 | 5/1980 | Townsend | 128/312 |
| 4,208,792 | 6/1980 | Ewig, Jr. | 30/341 |
| 4,368,734 | 1/1983 | Banko | 128/305 |
| 4,505,272 | 3/1985 | Utyamysher et al. | 128/305 |

FOREIGN PATENT DOCUMENTS

| | | | |
|---|---|---|---|
| 0741867 | 7/1980 | U.S.S.R. | 128/312 |
| 952990 | 3/1964 | United Kingdom | 30/242 |

Primary Examiner—John F. Niebling
Attorney, Agent, or Firm—Basile and Hanlon

[57] ABSTRACT

A ronguer or the like is formed with a pistol-shaped main frame assembly having a hollow, tubular cutting element releasably clamped at the forward end of the barrel of the frame. A rod slidably received in the barrel projects beyond the front end of the cutting element and has a rearwardly facing shoulder which can be drawn into the cutting element to shear bone or other material engaged between the shoulder and sharpened forward edge of the cutting element. The rod member may be selectively located in any of four rotative orientations for up-cutting, down-cutting or side-cutting from either side. The device is readily disassembled for cleaning and sterilization.

5 Claims, 2 Drawing Sheets

SURGICAL TOOL

BACKGROUND OF THE INVENTION

The present invention is directed to a surgical tool of the type employed for nibbling or shearing away small chips of bone during surgical procedures. Many specialized tools, such as ronguers, have been devised for this purpose.

Typically these tools have a pair of opposed surfaces, at least one of which is sharpened, which are moved toward each other by manually squeezing a pair of plier-like handles to grip and cut away that portion of a bone engaged between the opposed surfaces. See, for example, U.S. Pat. Nos. 1,040,523 to DeVilbiss and 4,201,213 to Townsend.

While many specialized instruments have been developed for this purpose, nearly all prior art instruments of this type known to me have one or more of the following drawbacks.

One of the most common problems encountered with prior art instruments is the fact that the cutting edge of the device is formed integrally upon one of the two shearing members, thus requiring specialized tools or techniques when it is necessary to resharpen the cutting edge. In the instrument of the present application, the cutting edge is formed on one end of a short length of metal tubing. This edge may be readily resharpened by chucking the cutting element in a rotary tool; however, this form of cutting element is so inexpensive it may be disposable after a single usage.

As with any surgical instrument, the capability of being thoroughly cleaned and sterilized is paramount. Because instruments of this type are made up of several moving parts, ease of assembly and disassembly is an important consideration which has not always received sufficient attention in prior art devices. The instrument to the present invention can be readily assembled and disassembled without the use of tools.

Typically, such instruments are of generally pistol shape with one of the opposed gripping surfaces at the end of the "barrel" and the other gripping surface provided by a generally radial recess in a rod which slidably projects from the end of the barrel. Depending upon the particular surgical procedure, the surgeon will select a ronguer called a "up-cutting" or "down-cutting" ronguer. An up-cutting ronguer finds the bone receiving recess in the cutting elements facing upwardly when the pistol-shaped instrument is held in its normal position; a down-cutting ronguer finds the recess on the bottom side of the cutting element. The instrument of the present invention enables the recess to be selectively located in an up-cutting, down-cutting or either side-cutting orientation; whereas in the prior art constructions, a single instrument usually provides only the capability of one type of cutting.

Further, the instrument of the present invention includes a relatively simple linkage actuating mechanism which provides a substantial mechanical advantage and also presents the capability of substituting or replacing the stationary grip portion of the handle to suit the surgeon.

SUMMARY OF THE INVENTION

In accordance with the present invention, a ronguer takes the form of a three-part fixed frame of generally pistol-shaped configuration. The basic portion of this three-piece frame is a central mounting section which has a forwardly projecting barrel threadably mounted at its forward end and a downwardly inclined handle or grip portion detachably mounted at its rearward end. The barrel bore has an enlarged diameter section at its front end, and a hollow tubular cutting element is inserted and axially seated in this enlarged diameter section to project forwardly beyond the front end of the barrel. The front end of the cutting element is sharpened to provide an annular cutting edge. The front end of the barrel is provided with some axially extending slots in a conically inclined surface at its front end. A collet-like nut may be threaded onto the front end of the barrel to radially compress the split sections to grip the cutting element in a collet-like chucking action. An elongate rod slidably passes through the front end of the mounting portion, the barrel and the cutting element and normally projects forwardly beyond the front end of the cutting element. An elongate radial recess is cut into one side of the rod just rearwardly of its forward end to provide a rearwardly facing shoulder.

A main pivot is seated in a bore at the front end of the mounting section and is provided with a diametral passage which slidably receives the rod member. The passage of the rod member through the main pivot retains the main pivot in its assembled position and a flatened side of this diametral passage may be selectively slidably engaged with any one of four flat surfaces on the side of the rod member to rotatably orient the rod member for up-cutting, down-cutting or side-cutting applications. A trigger-like actuating lever is pivotally supported on the main pivot and formed with a crank section extending radially from the pivot. A second pivot is threadably mounted on the rearward end of the rod member and a link is pivotally connected between this second pivot and the distal end of the crank on the actuating lever. A torsion spring biases the actuating lever to a forwardly extending position relative to the grip in which the linkage locates the rod member in a fully extended position with the rearwardly facing radial shoulder on the rod member spaced forwardly from the annular cutting edge of the cutting element. By squeezing the actuating lever toward the grip, the radial shoulder on the rod member is drawn axially into the front end of the cutting element, thereby shearing any bone or other matter engaged between the shoulder and the cutting edge.

Other objects and features of the invention will become apparent by reference to the following specification and to the drawings.

IN THE DRAWINGS

Figure 1:
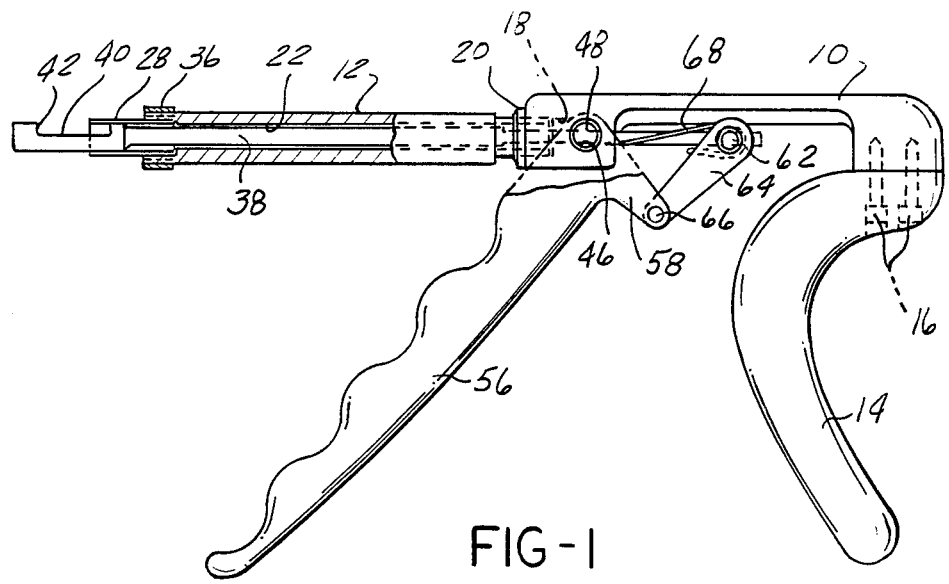
FIG. 1 is a side elevational view of the surgical tool showing the parts in their normal or ready position.
Figure 1A:
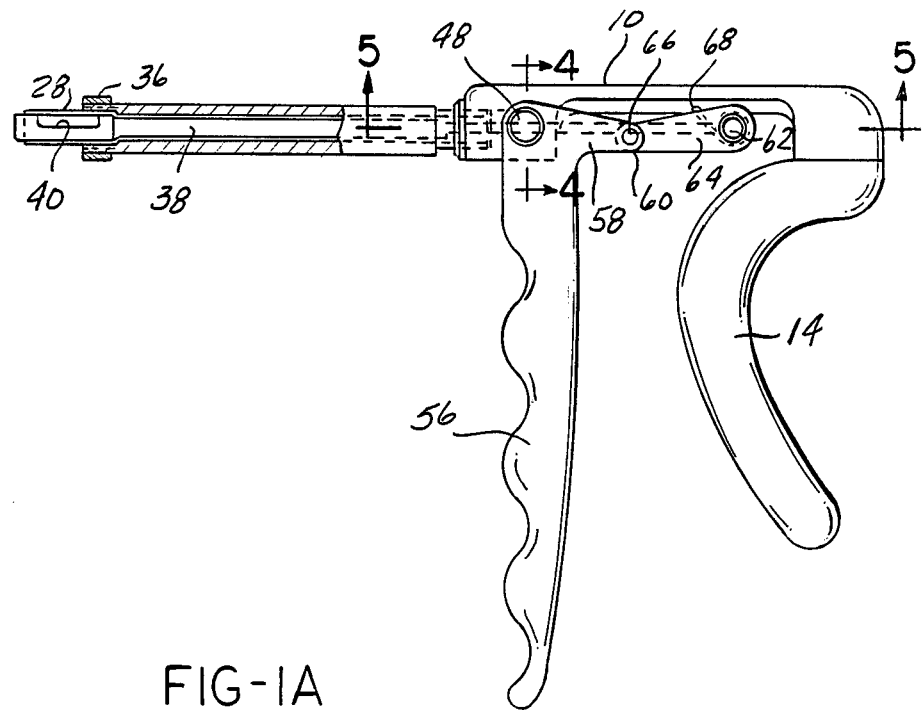
FIG. 1A is a view similar to FIG. 1, showing the parts in their actuated position.
Figure 2:
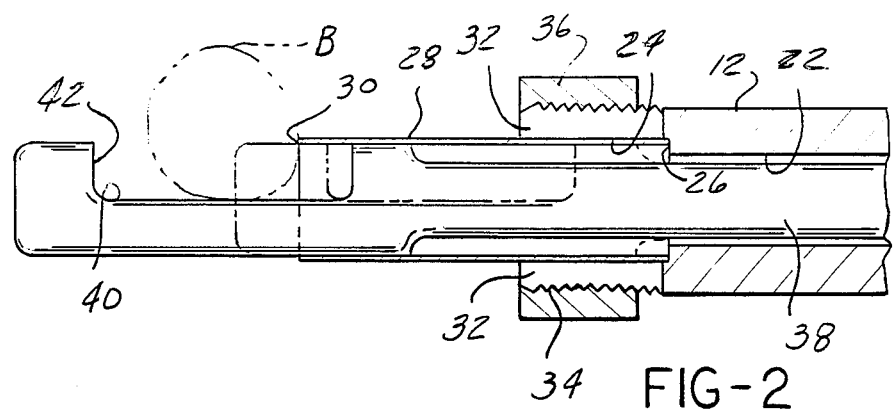
Figure 3:
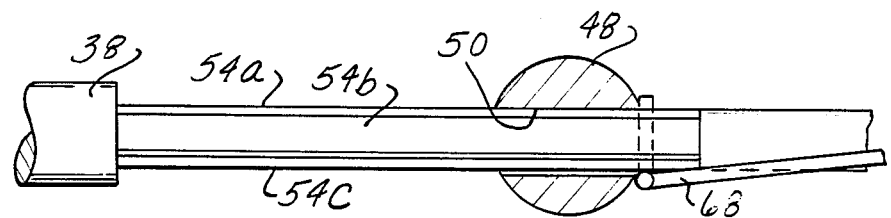
Figure 4:
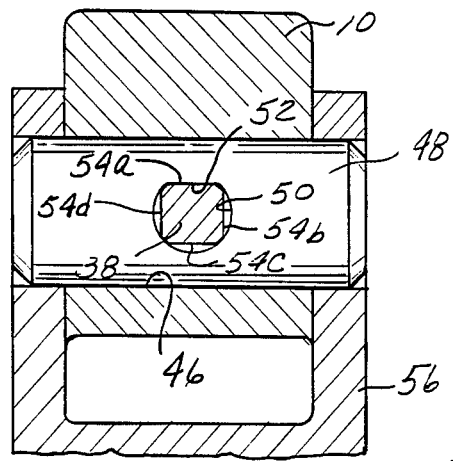

FIG. 2. is a detailed, cross-sectional view of the front end of the instrument of FIG. 1;

FIG. 3 is a detailed, side elevational view, partially in section, of a portion of the rod member and main pivot;

FIG. 4 is a partial, cross-sectional view taken on line 4—4 of FIG. 1A; and

Figure 5:
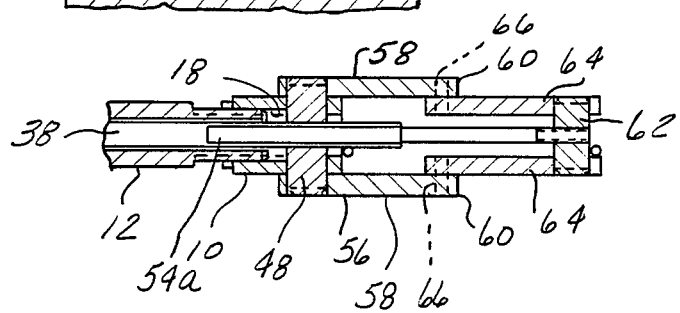

FIG. 5 is a detailed, cross-sectional view taken on the line 5—5 of FIG. 1A.

Referring first to FIGS. 1 and 1A, a surgical tool embodying the present invention includes a fixed frame of generally pistol-shaped configuration which is made up of a mounting section 10, a barrel 12 and a handle or grip portion 14 which may either be integrally formed with mounting portion 10 or detachably secured to the rearward portion of mounting portion 10 as by bolts 16 (FIG. 1). The forward end of mounting portion 10 is formed with a bore 18 into which barrel 12 is threadably received and held in position as by a lock nut 20.

Referring now to FIG. 2, it is seen that a bore 22 extends coaxially through barrel 12. An enlarged diameter portion 24 is formed at the forward end of bore 22 and terminates at its rearward end in a radial shoulder 26 which forms a seat for the inner end of a replaceable cutting element 28. Cutting element 28 is simply a short length of hollow metal tubing whose forward end is sharpened to provide an annular cutting edge 30 at the front end of the tube. The outer diameter of cutting element 28 is such that it is slidably received within the enlarged diameter section 24 of the bore in barrel 12. Axially extending slots, such as 32, are cut into the front end of barrel 12 and a frusto-conical section 34 is formed at the front end of the barrel. The barrel is externally threaded for a short distance from its front end and a collet-like nut 36, when threaded onto the front end of the barrel, radially clamps the slotted front end of the barrel firmly against the outer periphery of the cutting element in a collet-like chucking action.

An elongate rod member 38 extends entirely through bore 18 of mounting section 10, bore 22 of barrel 12 and through the hollow tubular cutting element 28. As best seen in FIG. 2, an elongate radial recess is 40 is formed on one side of the rod near its forward end to provide a rearwardly facing radial shoulder 42. Rod member 38 may be drawn to the right from the full-line position shown in FIG. 2 by a mechanism to be described below to shear chips or a section from a bone B trapped between radial shoulder 42 and cutting edge 30 as the shoulder 42 is drawn into the front end of tubular cutting element 28.

Referring now particularly to FIGS. 1, 4 and 5, it is seen that a bore 46 extends through mounting section 10 near its forward end. Bore 46 receives a main pivot 48 which, as best seen in FIG. 4, is formed with a diametral passage 50 which extends through the pivot. The cross-sectional configuration of this passage 50 as shown in FIG. 4 is generally circular with the exception of a flat section 52 at its upper side lying on a chord of the otherwise circular passage. As best seen in FIG. 3, rod member 38 is formed with a guide portion defined by four elongate flat sections 54a, 54b, 54c and 54d so that the guide portion constituted by the various flat sections 54a, etc. is of substantially square cross section as best appreciated from FIG. 4. The dimensions of the guide section of rod member 38 and diametral passage 50 through main pivot 48 are such that one of flat portions 54a, etc. is in sliding, face-to-face engagement with the flat section 52 of passage 50 so that rod 38 may thus be rotatively oriented at any one of four positions relative to mounting section 10. The specific orientation thus chosen determines whether recess 40 of rod member 38 faces upwardly for an up-cutting procedure or downwardly for down-cutting or to either side for side-cutting operations.

A trigger-like actuating lever 56 is bifurcated at its upper end and pivotally supported from main pivot 48. Crank arm portions 58 are integrally formed on lever 56 to extend radially from pivot 48 to a distal end 60.

Referring now to FIG. 5, a second pivot 62 is threadably received on the rearward end of rod member 38. A pair of links 64 are pivotally supported upon pivot 62 and are pivotally connected at their opposite ends to the distal end 60 of cranks 58 by a pair of pivots 66, one at each link 64. A torsion spring 68 has one end engaged on the top of a link 64, passes counterclockwise as viewed in FIGS. 1 and 1A around pivot 62 and then extends forwardly to have its forward end engaged under rod 38 adjacent main pivot 48 as best seen in FIG. 3. The torsion spring biases links 64 to the position shown in FIG. 1 which in turn positions the actuating lever in its extended or cocked position shown in FIG. 1, the linkage in turn positioning rod member 38 in a forward, extended position in which radial shoulder 42 is spaced forwardly from the cutting edge of cutting element 28. By manually squeezing actuating lever 56 from the FIG. 1 position to the FIG. 1A position, rod member 38 is drawn into the forward end of cutting element 28 to perform the cutting action.

The instrument may be readily disassembled by unthreading barrel 12 from mounting section 10 and unthreading nut 36 to permit removal of cutting element 28 from the barrel. Rod 38 is then unthreaded from pivot 62 and withdrawn forwardly from mounting section 10, thus permitting main pivot 48 to be withdrawn from bore 46 and laterally from lever 56. Removal of pivots 66 and spring 68 plus screws 16, if necessary, completes the disassembly.

While one embodiment of the invention has been described in detail, it will be apparent to those skilled in the art that the disclosed embodiment may be modified. Therefore, the foregoing description is to be considered exemplary rather than limiting, and the true scope of the invention is that defined in the following claims.

What is claimed is:

1. A surgical tool comprising a pistol-like frame including a grip portion and an elongate hollow tubular barrel portion projecting forwardly from the upper end of said grip portion, a hollow tubular cutting element mounted in the forward end of said barrel portion and projecting forwardly therefrom, said cutting element having a sharpened annular cutting edge at its forward end, an elongate rod member passing longitudinally through said cutting element and said barrel portion and mounted for forward and rearward sliding movement therein, a main pivot received in said barrel portion, said main pivot defining a main pivot axis extending normal to and intersecting the longitudinal axis of said rod member, said main pivot having a diametral passage therethrough slidably receiving said rod member, a trigger-like actuating member mounted upon said main pivot for pivotal movement relative to said frame about said pivot axis toward and away from said grip portion, linkage means including a link coupled at one end to said rod member and pivotally coupled at its opposite end to said actuating member to locate said rod member in a forwardly projected, ready position when said actuating member is pivoted about said main pivot axis to a first extended position relative to said grip portion and to locate said rod member in a rearwardly withdrawn, actuated position when said actuating member is pivoted about said main pivot axis to a second retracted position relative to said grip portion, spring means biasing said actuating member to said first position, and means defining a recess in one side of said rod member adjacent the forward end thereof having a rearwardly facing shoulder at the forward end thereof located in forwardly spaced relationship to said cutting edge when said rod member is in said ready position and withdrawn into the interior of said cutting element when said rod member is in said actuated position.

2. The invention defined in claim 1 wherein said barrel portion of said frame comprises means defining a transverse bore adapted to slidably receive said main pivot, said main pivot being retained in said transverse bore by said rod member.

3. The invention defined in claim 1 wherein said rod member includes a longitudinal guide section intermediate its ends movable within said diametral passage upon movement of said rod member between its ready and actuated positions, said guide portion having a plurality of flat surfaces thereon lying in respective planes parallel to the longitudinal axis of said rod member and extending the entire length of said guide portion, said diametral passage having a flat side wall portion slidably engageable with any selected one of said flat surfaces of said guide portion to thereby rotatively orient said recess in said rod member in a selected rotative orientation relative to said frame.

4. The invention defined in claim 1 wherein said linkage means further comprises crank means fixed on said actuating member and extending radially from said main pivot to a distal end located below and rearwardly of said main pivot and forwardly of the pivotal connection between said one end of said link and said rod member, said link being pivotally connected at its other end to the distal end of said crank.

5. The invention defined in claim 1 wherein said barrel portion comprises a barrel section having a central, longitudinal bore therethrough slidably receiving said rod member, said bore having an enlarged diameter section extending inwardly from the front end of said barrel section to terminate at a forwardly facing shoulder, said cutting member being insertable into said enlarged diameter section of said bore and having a rearward end adapted to be axially seated against said forwardly facing shoulder, and means for releasably clamping said cutting member in said enlarged diameter section of said bore.

* * * * *